US012569206B2

(12) United States Patent
Xiang

(10) Patent No.: US 12,569,206 B2
(45) Date of Patent: Mar. 10, 2026

(54) SYSTEMS, DEVICES, AND METHODS FOR SCANNING PARAMETER DETERMINATION

(71) Applicant: SHANGHAI UNITED IMAGING HEALTHCARE CO., LTD., Shanghai (CN)

(72) Inventor: Qiujing Xiang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 685 days.

(21) Appl. No.: 18/149,031

(22) Filed: Dec. 30, 2022

(65) Prior Publication Data

US 2024/0023909 A1 Jan. 25, 2024

(30) Foreign Application Priority Data

Jul. 22, 2022 (CN) .......................... 202210866179.3

(51) Int. Cl.
| | |
|---|---|
| *A61B 6/00* | (2024.01) |
| *A61B 6/03* | (2006.01) |
| *G06T 7/00* | (2017.01) |

(52) U.S. Cl.
CPC ............ *A61B 6/032* (2013.01); *G06T 7/0012* (2013.01); *A61B 6/48* (2013.01)

(58) Field of Classification Search
CPC ........... A61B 6/032; A61B 6/48; A61B 6/545; A61B 6/465; A61B 5/055; G06T 7/0012; G16H 10/20; G16H 15/00; G16H 30/20; G06F 3/011; G06F 3/04817; G06F 3/0484; G06F 3/0488; G06F 9/451
See application file for complete search history.

(56) References Cited

U.S. PATENT DOCUMENTS

2019/0231224 A1* 8/2019 Rupcich ................. A61B 6/032

\* cited by examiner

*Primary Examiner* — Courtney D Thomas
(74) *Attorney, Agent, or Firm* — METIS IP LLC

(57) ABSTRACT

The present disclosure provides systems, devices, and methods for scanning parameter determination. The systems may display, via a user terminal, a user interface including one or more input items for a user to input clinical information relating to a target subject. The clinical information may at least include symptom information. The systems may receive, from the user terminal, the clinical information relating to the target subject. The systems may further determine, based on the clinical information using a scanning parameter determination model, recommended values of scanning parameters to be used in a scan of the target subject. The scanning parameter determination model may be a trained machine learning model.

20 Claims, 9 Drawing Sheets

100

<u>300</u>

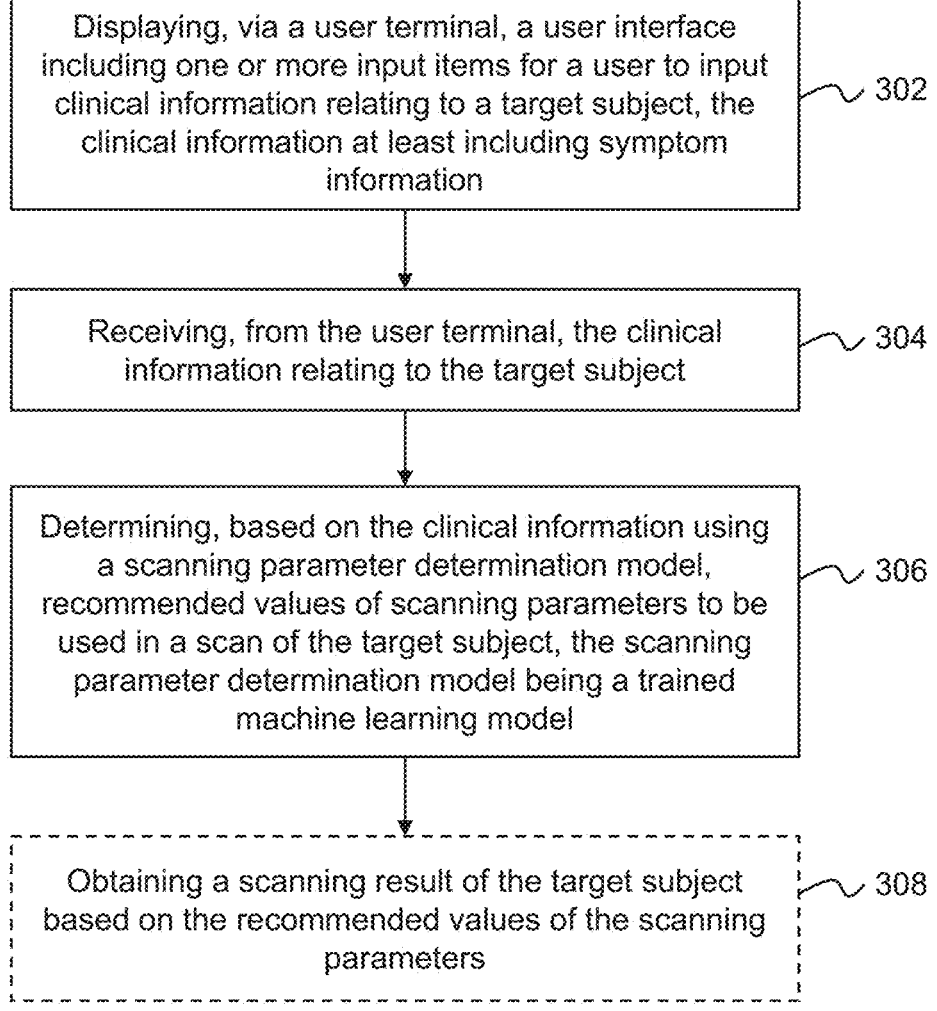

Displaying, via a user terminal, a user interface including one or more input items for a user to input clinical information relating to a target subject, the clinical information at least including symptom information ~∿ 302

Receiving, from the user terminal, the clinical information relating to the target subject ~∿ 304

Determining, based on the clinical information using a scanning parameter determination model, recommended values of scanning parameters to be used in a scan of the target subject, the scanning parameter determination model being a trained machine learning model ~∿ 306

Obtaining a scanning result of the target subject based on the recommended values of the scanning parameters ~∿ 308

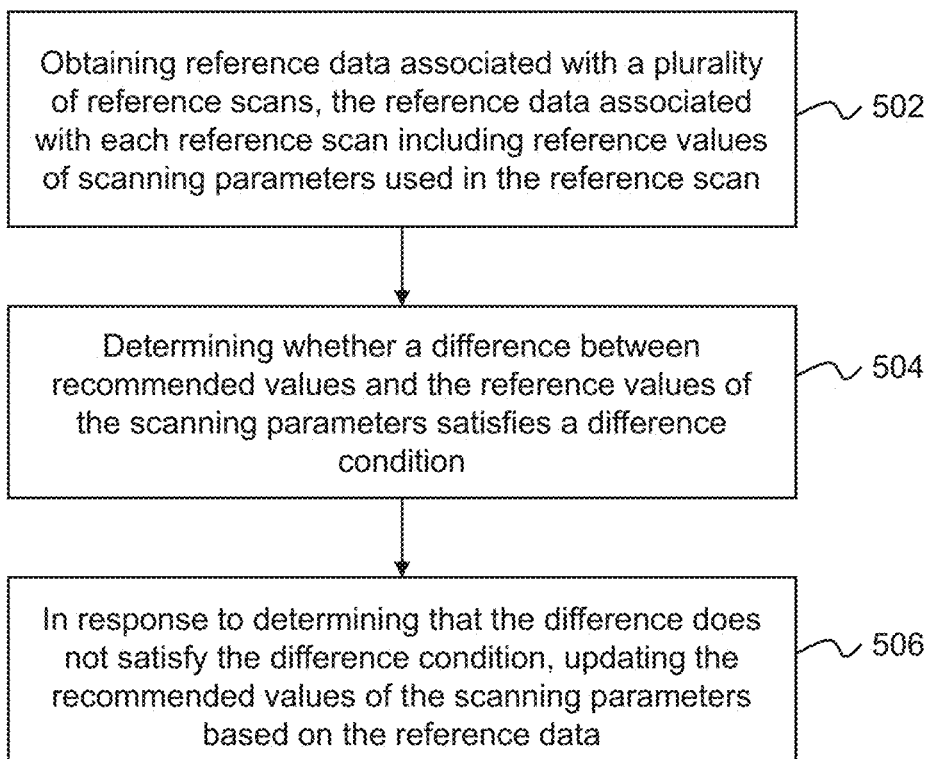

Obtaining reference data associated with a plurality of reference scans, the reference data associated with each reference scan including reference values of scanning parameters used in the reference scan — 502

Determining whether a difference between recommended values and the reference values of the scanning parameters satisfies a difference condition — 504

In response to determining that the difference does not satisfy the difference condition, updating the recommended values of the scanning parameters based on the reference data — 506

Symptom Information:

7462

Diagnostic Information:

7464

Location Information:

7466

748

START

750

730

720

710

800

SYSTEMS, DEVICES, AND METHODS FOR SCANNING PARAMETER DETERMINATION

CROSS-REFERENCE TO RELATED APPLICATIONS

This application claims priority to Chinese Patent Application No. 202210866179.3, filed on Jul. 22, 2022, the contents of which are incorporated herein by reference.

TECHNICAL FIELD

The present disclosure generally relates to imaging technology, and more particularly, relates to systems, devices, and methods for scanning parameter determination.

BACKGROUND

In recent years, medical devices have been widely used in the diagnosis and treatment. However, to obtain a medical image satisfying user requirement(s), a plurality of scanning parameters need to be manually determined. For example, when a magnetic resonance (MR) system is used to scan a patient, a scanning technician needs to spend a lot of time scheduling a plurality of scanning procedures to satisfy requirement(s) of a clinician, which is time-consuming, labor-intensive, and inefficient. Therefore, it is desirable to provide systems, devices, and methods for scanning parameter determination, which can efficiently and automatically determine the scanning parameters of the medical devices.

SUMMARY

In one aspect of the present disclosure, a method for scanning parameter determination is provided. The method may be implemented on a computing device having at least one processor and at least one storage device. The method may include displaying, via a user terminal, a user interface including one or more input items for a user to input clinical information relating to a target subject. The clinical information may at least include symptom information. The method may include receiving, from the user terminal, the clinical information relating to the target subject. The method may further include determining, based on the clinical information using a scanning parameter determination model, recommended values of scanning parameters to be used in a scan of the target subject. The scanning parameter determination model may be a trained machine learning model.

In some embodiments, the clinical information may further include at least one of diagnostic information of the target subject, location information of a region of interest of the target subject, or profile information of the target subject.

In some embodiments, the method may further include obtaining a scanning result of the target subject based on the recommended values of the scanning parameters; determining whether the scanning result satisfies a scanning condition; and in response to determining that the scanning result does not satisfy the scanning condition, updating the clinical information based on the scanning result.

In some embodiments, the method may further include determining, during the scan of the target subject, whether an abnormal condition occurs.

In some embodiments, the determining whether an abnormal condition occurs may include obtaining one or more detection images of the target subject captured during the scan of the target subject; obtaining a determination result by determining whether the one or more detection images of the target subject satisfy the abnormal condition; and determining whether the abnormal condition occurs based on the determination result.

In some embodiments, the scan of the target subject may be divided into a plurality of sub-scans, and each of the plurality of sub-scans may correspond to at least one of the one or more detection images.

In some embodiments, the method may further include, in response to determining that the abnormal condition occurs, determining a processing strategy of the abnormal condition based on the one or more detection images of the target subject.

In some embodiments, the method may further include obtaining reference data associated with a plurality of reference scans, the reference data associated with each reference scan including reference values of the scanning parameters used in the reference scan; determining whether a difference between the recommended values and the reference values of the scanning parameters satisfies a difference condition; and in response to determining that the difference does not satisfy the difference condition, updating the recommended values of the scanning parameters based on the reference data.

In some embodiments, the scanning parameter determination model may include a first scanning parameter determination model and a second scanning parameter determination model, and the scanning parameters to be used may include one or more first scanning parameters of a first type and one or more second scanning parameters of a second type. The determining recommended values of scanning parameters to be used in a scan of the target subject may include determining the recommended value of each first scanning parameter based on a first portion of the clinical information using the first scanning parameter determination model; and determining the recommended value of each second scanning parameter based on a second portion of the clinical information using the second scanning parameter determination model.

In some embodiments, the scanning parameter determination model may be generated according to a process including obtaining a plurality of training samples, each of the plurality of training samples including sample clinical information relating to a sample subject and ground truth values of the scanning parameters; and generating the scanning parameter determination model by training an initial model using the plurality of training samples.

In another aspect of the present disclosure, a system for scanning parameter determination is provided. The system may include at least one storage device including a set of instructions; and at least one processor configured to communicate with the at least one storage device. When executing the set of instructions, the at least one processor may be configured to direct the system to perform operations. The operations may include displaying, via a user terminal, a user interface including one or more input items for a user to input clinical information relating to a target subject. The clinical information may at least include symptom information. The operations may include receiving, from the user terminal, the clinical information relating to the target subject. The operations may further include determining, based on the clinical information using a scanning parameter determination model, recommended values of scanning parameters to be used in a scan of the target subject. The scanning parameter determination model may be a trained machine learning model.

In still another aspect of the present disclosure, a non-transitory computer readable medium is provided. The non-transitory computer readable medium may include executable instructions that, when executed by at least one processor, direct the at least one processor to perform a method. The method may include displaying, via a user terminal, a user interface including one or more input items for a user to input clinical information relating to a target subject. The clinical information may at least include symptom information. The method may include receiving, from the user terminal, the clinical information relating to the target subject. The method may further include determining, based on the clinical information using a scanning parameter determination model, recommended values of scanning parameters to be used in a scan of the target subject. The scanning parameter determination model may be a trained machine learning model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3 is a flowchart illustrating an exemplary process for obtaining a scanning result of a target subject according to some embodiments of the present disclosure;

FIG. 5 is a flowchart illustrating an exemplary process for updating recommended values of scanning parameters according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 1:
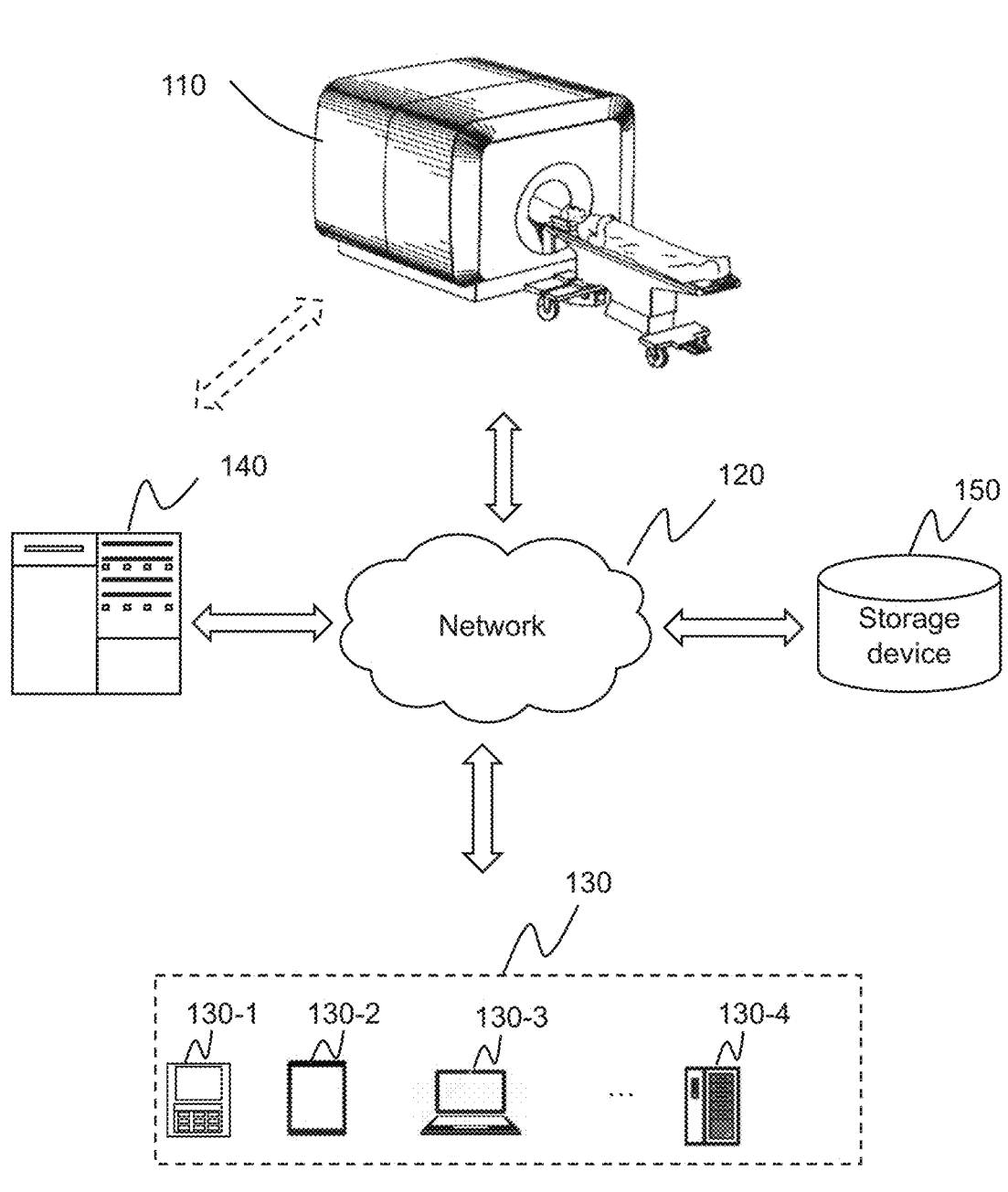
FIG. 1 is a schematic diagram illustrating an exemplary imaging system according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processing device 140 as illustrated in FIG. 1) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included in programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, the expression "A and/or B" includes only A, only B, or both A and B. The character "/" includes one of the associated listed terms. The term "multiple" or "a/the plurality of" in the present disclosure refers to two or more. The terms "first," "second," and "third," etc., are used to distinguish similar objects and do not represent a specific order of the objects.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

When a medical device is used to scan a subject, a plurality of scanning parameters need to be determined before the scan is performed, which is time-consuming, labor-intensive, and inefficient. In addition, due to the complexity of the medical device, the medical device is directed by a scanning technician other than a clinician. The clinician provides scanning requirement(s) to the scanning technician, and the scanning technician determines the plurality of scanning parameters based on the scanning requirement(s). Therefore, the clinician can obtain a scanning result after the scan of the subject and make a diagnosis based on the scanning result. If the scanning result does not satisfy the scanning requirement(s), the scan needs to be re-performed on the subject, which reduces the efficiency of the scan and prolongs a time period that the subject is exposed to the radiation.

In order to reduce labor consumption and improve the efficiency and accuracy of scanning parameter determination, the present disclosure provides systems, devices, and methods for scanning parameter determination. The systems may display, via a user terminal, a user interface including one or more input items for a user to input clinical information relating to a target subject. The clinical information may at least include symptom information. The systems may receive, from the user terminal, the clinical information relating to the target subject. The systems may further determine, based on the clinical information using a scanning parameter determination model, recommended values of scanning parameters to be used in a scan of the target subject. Therefore, the recommended values of the scanning parameters can be determined intelligently and automatically, which can reduce time and/or labor consumption, and improve the efficiency and accuracy of scanning parameter determination.

In addition, by introducing a machine learning model (i.e., the scanning parameter determination model), the system can automatically determine and/or update the recommended values of the scanning parameters. Moreover, possible abnormal conditions that occur during the scan may be detected and processed automatically. Therefore, the user does not need to constantly monitor the implementation of the scan, which can avoid poor scanning results caused by differences in the level of the users, thereby improving the reliability and consistency of scanning results.

In some embodiments, the clinical information may be input by a clinician having direct contact with patients rather than being involved with theoretical or laboratory studies or medical scanning settings. For example, when the target subject sees the clinician, the clinician may inquire symptoms and other information of the target subject, and input the information into the input items. In this way, the methods for scanning parameter determination may be performed based on information input by the clinician without the participation of any scanning technician, which improves the efficiency of scanning parameter determination and ensures that the determined scanning parameters meet the clinician's requirement.

FIG. 1 is a schematic diagram illustrating an exemplary imaging system 100 according to some embodiments of the present disclosure. As shown in FIG. 1, the imaging system 100 may include a medical device 110, a network 120, one or more terminals 130, a processing device 140, and a storage device 150. In some embodiments, the medical device 110, the processing device 140, the storage device 150, and/or the terminal(s) 130 may be connected to and/or communicate with each other via a wireless connection, a wired connection, or a combination thereof. The connection between the components in the imaging system 100 may be variable. Merely by way of example, the medical device 110 may be connected to the processing device 140 through the network 120, as illustrated in FIG. 1. As another example, the medical device 110 may be connected to the processing device 140 directly. As a further example, the storage device 150 may be connected to the processing device 140 through the network 120, as illustrated in FIG. 1, or connected to the processing device 140 directly.

The medical device 110 may be configured to generate or provide image data by scanning a subject or at least a part of the subject. In some embodiments, the medical device 110 may include a single modality imaging device. For example, the medical device 110 may include a computed tomography (CT) device, a magnetic resonance imaging (MRI) device, a positron emission tomography (PET) device, an X-ray imaging device, a single-photon emission computed tomography (SPECT) device, an ultrasound device, etc. In some embodiments, the medical device 110 may include a multi-modality imaging device. Exemplary multi-modality imaging devices may include a positron emission tomography-computed tomography (PET-CT) device, a positron emission tomography-magnetic resonance imaging (PET-MRI) device, a computed tomography-magnetic resonance imaging (CT-MRI) device, etc. The multi-modality scanner may perform multi-modality imaging simultaneously or in sequence. For example, the PET-CT device may generate structural X-ray CT image data and functional PET image data simultaneously or in sequence. The PET-MRI device may generate MRI data and PET data simultaneously or in sequence.

Merely by way of example, the medical device 110 may be the MRI device. The MRI device may be configured to scan the subject (or a part of the subject) to acquire scan data, such as MR signals associated with the subject. For example, the MRI device may detect a plurality of MR signals by applying an MR sequence on the subject. In some embodiments, the MRI device may include, for example, a magnetic body, a gradient coil assembly, a radiofrequency (RF) coil assembly, etc. In some embodiments, the MRI device may be a permanent magnet MR scanner, a superconducting electromagnet MR scanner, a resistive electromagnet MR scanner, etc., according to types of the magnetic body. In some embodiments, the MRI device may be a high-field MR scanner, a mid-field MR scanner, a low-field MR scanner, etc., according to the intensity of the magnetic field.

The magnetic body may generate a first magnetic field (also referred to as a main magnetic field) for polarizing the subject to be scanned. The gradient coil assembly may generate a second magnetic field (also referred to as a gradient magnetic field). The gradient coil assembly may include X-gradient coils, Y-gradient coils, and Z-gradient coils. The gradient coil assembly may generate one or more magnetic field gradient pulses to the main magnetic field in the X direction (Gx), the Y direction (Gy), and the Z direction (Gz) to encode the spatial information of the subject. The RF coil assembly may include a plurality of RF coils. The RF coils may include one or more RF transmit coils and/or one or more RF receiver coils. The RF transmit coil(s) may transmit RF pulses to the subject. Under the coordinated action of the main magnetic field, the gradient magnetic field, and the RF pulses, a pulse sequence (also referred to as a scanning sequence) may be applied to the subject to excite one or more MR signals relating to the subject. The RF receiver coils may acquire MR signals from the subject according to the pulse sequence. The MR signals may be processed using a transform operation (e.g., Fourier Transform) to fill a k-space to obtain k-space data. The k-space data may be reconstructed according to an MR reconstruction algorithm (e.g., a back projection technique, an iteration reconstruction technique) to obtain an MR image of the subject.

The subject may include patients or other experimental subjects (e.g., experimental mice or other animals). In some embodiments, the subject may be a patient or a specific portion, organ, and/or tissue of the patient. For example, the subject may be a patient to be scanned by the medical device 110. As another example, the subject may include the head, the neck, the thorax, the heart, the stomach, a blood vessel, soft tissue, a tumor, nodules, or the like, or any combination thereof. In some embodiments, the subject may be non-biological. For example, the subject may include a phantom, a man-made object, etc. The terms "object" and "subject" are used interchangeably in the present disclosure.

The network 120 may include any suitable network that can facilitate the exchange of information and/or data for the imaging system 100. In some embodiments, one or more components (e.g., the medical device 110, the terminal(s) 130, the processing device 140, the storage device 150, etc.) of the imaging system 100 may communicate information and/or data with one or more other components of the imaging system 100 via the network 120. For example, the processing device 140 may obtain image data from the medical device 110 via the network 120. As another example, the processing device 140 may obtain user instructions from the terminal(s) 130 via the network 120. In some embodiments, the network 120 may include one or more network access points.

The terminal(s) 130 may include a mobile device 130-1, a tablet computer 130-2, a laptop computer 130-3, a desktop computer 130-4, or the like, or any combination thereof. In some embodiments, the mobile device 130-1 may include a smart home device, a wearable device, a mobile device, a virtual reality device, an augmented reality device, or the like, or any combination thereof. In some embodiments, the terminal(s) 130 may include a processing unit, a display unit, a sensing unit, an input/output (I/O) unit, a storage unit, etc. Exemplary display units may include a liquid crystal display (LCD), a light-emitting diode (LED)-based display, a flat panel display, a curved screen, a television device, a cathode ray tube (CRT), or the like, or a combination thereof. In some embodiments, the terminal(s) 130 may be part of the processing device 140.

The processing device 140 may process data and/or information obtained from one or more components (the medical device 110, the terminal(s) 130, and/or the storage device 150) of the imaging system 100. For example, the processing device 140 may display, via a user terminal (e.g., the terminal(s) 130), a user interface including one or more input items for a user to input clinical information relating to a target subject. The clinical information may at least include symptom information. As another example, the processing device 140 may receive, from the user terminal (e.g., the terminal(s) 130), the clinical information relating to the target subject. As still another example, the processing device 140 may determine, based on the clinical information using a scanning parameter determination model, recommended values of scanning parameters to be used in a scan of the target subject. The scanning parameter determination model may be a trained machine learning model. As yet another example, the processing device 140 may obtain a scanning result of the target subject based on the recommended values of the scanning parameters. In some embodiments, the processing device 140 may be a single server or a server group. The server group may be centralized or distributed. In some embodiments, the processing device 140 may be local or remote. In some embodiments, the processing device 140 may be implemented on a cloud platform.

In some embodiments, the processing device 140 may be implemented by a computing device. For example, the computing device may include a processor, a storage, an input/output (I/O), and a communication port. The processor may execute computer instructions (e.g., program codes) and perform functions of the processing device 140 in accordance with the techniques described herein. The computer instructions may include, for example, routines, programs, objects, components, data structures, procedures, modules, and functions, which perform particular functions described herein. In some embodiments, the processing device 140, or a portion of the processing device 140 may be implemented by a portion of the terminal(s) 130.

The storage device 150 may store data/information obtained from the medical device 110, the terminal(s) 130, and/or any other component of the imaging system 100. In some embodiments, the storage device 150 may include a mass storage, a removable storage, a volatile read-and-write memory, a read-only memory (ROM), or the like, or any combination thereof. In some embodiments, the storage device 150 may store one or more programs and/or instructions to perform exemplary methods described in the present disclosure.

In some embodiments, the storage device 150 may be connected to the network 120 to communicate with one or more other components in the imaging system 100 (e.g., the processing device 140, the terminal(s) 130, etc.). One or more components in the imaging system 100 may access the data or instructions stored in the storage device 150 via the network 120. In some embodiments, the storage device 150 may be directly connected to or communicate with one or more other components in the imaging system 100 (e.g., the processing device 140, the terminal(s) 130, etc.). In some embodiments, the storage device 150 may be part of the processing device 140.

In some embodiments, the imaging system 100 may include one or more additional components and/or one or more components of the imaging system 100 described above may be omitted. Additionally or alternatively, two or more components of the imaging system 100 may be integrated into a single component. A component of the imaging system 100 may be implemented on two or more sub-components.

Figure 2:
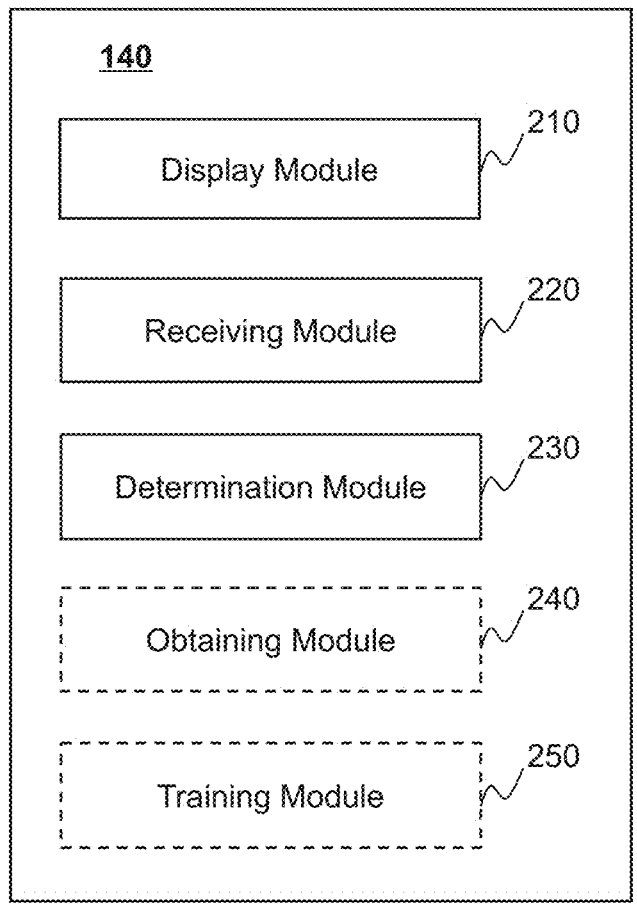
FIG. 2 is a block diagram illustrating an exemplary processing device according to some embodiments of the present disclosure.

FIG. 2 is a block diagram illustrating an exemplary processing device 140 according to some embodiments of the present disclosure. In some embodiments, the modules illustrated in FIG. 2 may be implemented on the processing device 140. In some embodiments, the processing device 140 may be in communication with a computer-readable storage medium (e.g., the storage device 150 illustrated in FIG. 1) and execute instructions stored in the computer-readable storage medium. The processing device 140 may include a display module 210, a receiving module 220, and a determination module 230.

The display module 210 may be configured to display, via a user terminal, a user interface including one or more input items for a user to input clinical information relating to a target subject. The clinical information may at least include symptom information. More descriptions regarding the display of the user interface may be found elsewhere in the present disclosure. See, e.g., operation 302 and relevant descriptions thereof.

The receiving module 220 may be configured to receive, from the user terminal, the clinical information relating to the target subject. More descriptions regarding the receiving of the clinical information may be found elsewhere in the present disclosure. See, e.g., operation 304 and relevant descriptions thereof.

The determination module 230 may be configured to determine, based on the clinical information using a scanning parameter determination model, recommended values of scanning parameters to be used in a scan of the target subject. The scanning parameter determination model may be a trained machine learning model. More descriptions regarding the determination of the recommended values of the scanning parameters may be found elsewhere in the present disclosure. See, e.g., operation 306 and relevant descriptions thereof.

In some embodiments, the processing device 140 may further include an obtaining module 240 and a training module 250.

The obtaining module 240 may be configured to obtain a scanning result of the target subject based on the recommended values of the scanning parameters. More descriptions regarding the obtaining of the scanning result of the target subject may be found elsewhere in the present disclosure. See, e.g., operation 308 and relevant descriptions thereof.

The training module 250 may be configured to generate the scanning parameter determination model. The scanning parameter determination model may be configured to determine the recommended values of the scanning parameters to be used in the scan of the target subject based on a model input. More descriptions regarding the receiving of the clinical information may be found elsewhere in the present disclosure. See, e.g., operations 402 and 404, and relevant descriptions thereof.

It should be noted that the above descriptions of the processing device 140 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the processing device 140 may include one or more other modules. For example, the processing device 140 may include a storage module to store data generated by the modules in the processing device 140. In some embodiments, any two of the modules may be combined as a single module, and any one of the modules may be divided into two or more units.

In some embodiments, the training module 250 and other modules described above may be implemented on different computing devices. Merely by way of example, the training module 250 may be implemented on a computing device of a vendor of the scanning parameter determination model, while the other modules described above may be implemented on a computing device of a user of the scanning parameter determination model.

FIG. 3 is a flowchart illustrating an exemplary process 300 for obtaining a scanning result of a target subject according to some embodiments of the present disclosure. In some embodiments, process 300 may be implemented in the imaging system 100 illustrated in FIG. 1. For example, the process 300 may be stored in the storage device 150 in the form of instructions (e.g., an application), and invoked and/or executed by the processing device 140. The operations of the illustrated process presented below are intended to be illustrative. In some embodiments, the process 300 may be accomplished with one or more additional operations not described, and/or without one or more of the operations discussed. Additionally, the order in which the operations of the process 300 as illustrated in FIG. 3 and described below is not intended to be limiting.

In some embodiments, to obtain a scanning result of a target subject, scanning parameters to be used in a scan of the target subject should be determined. For example, when an MRI system is used to scan the target subject, different scanning procedures may be manually determined for different scanning parts of the target subject. Each scanning procedure may include a plurality of scanning protocols for acquiring different information, for example, a portion of the plurality of scanning protocols are used to obtain anatomical structure information of the scanning part, a portion of the plurality of scanning protocols are used to quantitatively determine physiological and/or functional values of tissues in the scanning part, a portion of the plurality of scanning protocols are used to determine a contrast between a lesion and the surrounding tissues under an injection of a contrast agent, etc. A scanning technician needs to schedule one or more scanning protocols based on clinical requirement(s) provided by another user (e.g., a clinician). In addition, during the scan of the target subject, the scanning technician needs to pay attention to the cooperation of the target subject, such as, whether the target subject keeps still, whether the target subject remains breath-holding, whether the target subject keeps breathing, whether the target subject keeps the heart rate stable, etc., which seriously affects the scanning result. Further, the scanning technician needs to update the one or more scanning protocols based on a comprehensive situation (e.g., the cooperation of the target subject) of the scan, which is time-consuming, labor-intensive, and inefficient. In order to reduce time and/or labor consumption and improve the efficiency of scanning parameter determination, the process 300 may be performed.

For illustration purposes, the MRI system may be taken as an example. It should be noted that the process 300 may be implemented in other imaging systems, such as a CT system, a PET system, an X-ray imaging system, an ultrasonic imaging system, a PET-MRI system, or the like.

In 302, the processing device 140 (e.g., the display module 210) may display, via a user terminal, a user interface including one or more input items for a user to input clinical information relating to a target subject. The clinical information may at least include symptom information.

Figure 7:
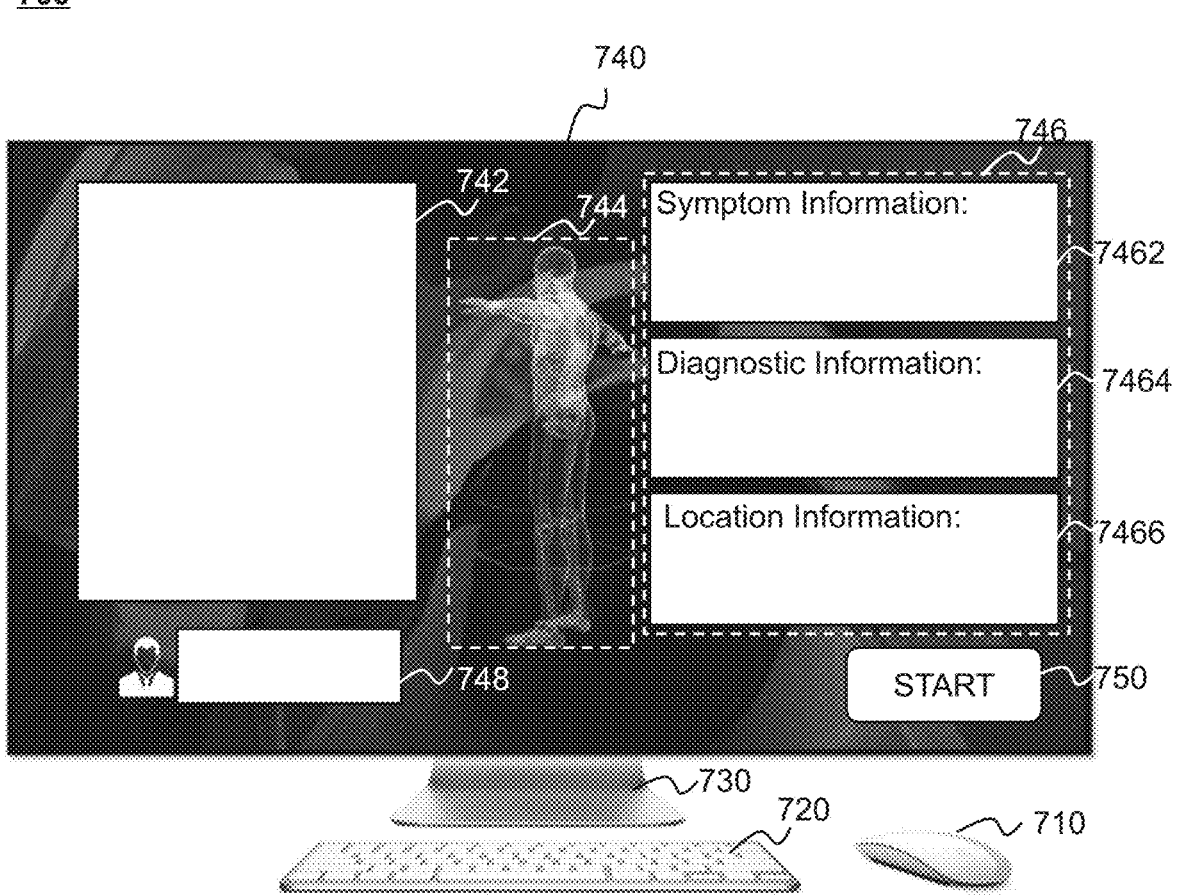
FIG. 7 is a schematic diagram illustrating an exemplary user terminal according to some embodiments of the present disclosure.

In some embodiments, the user interface may be displayed by the user terminal (e.g., the terminal(s) 130). For example, the user interface may be displayed by the user terminal via an application or a website. As another example, the user interface may be an interface displayed on a projection surface projected by a projection device or an augmented reality (AR) device. The user terminal may be connected to and/or communicate with other components (e.g., the medical device 110, the processing device 140, and/or the storage device 150) of the imaging system 100. In some embodiments, the user terminal may include an input device (e.g., a mouse 710 and a keyboard 720 as illustrated in FIG. 7), an output device (e.g., a display device 730 as illustrated in FIG. 7), etc., as described elsewhere in the present disclosure (e.g., FIGS. 1 and 7, and the descriptions thereof).

In some embodiments, the user interface may facilitate communication between the user (e.g., a clinician) and one or more components in the imaging system 100. For example, the user may input the clinical information relating to the target subject to the user terminal through the one or more input items of the user interface. In some embodiments, the user may be a clinician having direct contact with patients rather than being involved with theoretical or laboratory studies or medical scanning settings. For example, when the target subject sees the clinician, the clinician may inquire symptoms and other information of the target subject, and input the information into the input items. In this way, the process 300 may be performed based on information input by the clinician without requiring a scanning technician to set scanning parameters, which improves the efficiency of scanning parameter determination.

In some embodiments, each of the one or more input items may be presented on the user interface as a text box, a button, an icon, etc. Accordingly, the user may input the clinical information relating to the target subject through the text box, the button, the icon, etc. For example, the user may input the clinical information into the user terminal by inputting text indicating the clinical information into the text box. As another example, the user may input the clinical information into the user terminal by clicking or touching the button and/or icon representing the clinical information. In some embodiments, the processing device 140 may automatically input the one or more input items. For example, after the target subject is identified, the processing device 140 may retrieve the clinical information relating to the target subject from a storage device (e.g., the storage device 150, a storage device connected to a hospital information system (HIS), a storage device connected to a radiology information system (RIS), etc.) that stores the clinical information relating to the target subject, and input the one or more input items. In some embodiments, the user may check and/or update the input clinical information.

In some embodiments, the user may input the clinical information via typing, speaking, touching, or the like, or any combination thereof.

The target subject may refer to a subject to be scanned by a medical device (e.g., the medical device 110). More descriptions regarding the subject may be found elsewhere in the present disclosure. See, e.g., FIG. 1 and relevant descriptions thereof.

The clinical information may include any information used for medical diagnosis and/or treatment. In some embodiments, the clinical information may at least include symptom information. The symptom information may indicate subjective abnormal sensation(s) and/or objective morbid change(s) caused by disease(s). In some embodiments, the symptom information may include one or more signs and/or one or more symptoms. A sign may refer to a condition that is observed or detectable. For example, the sign may include a higher or lower temperature than a normal temperature (e.g., a temperature range from 36 to 37 degrees centigrade), a higher or lower blood pressure than a normal blood pressure (e.g., a systolic blood pressure range from 90 to 140 millimeters of mercury (mmHg), a diastolic blood pressure from 60 to 90 mmHg), an abnormality showing on a medical scan, etc. A symptom may refer to a condition that is felt by the target subject. For example, the symptom may include a dizziness, a pain (e.g., a headache) of the target subject, etc.

In some embodiments, the clinical information may further include diagnostic information of the target subject, location information of a region of interest (ROI) of the target subject, profile information of the target subject, or the like, or any combination thereof. The diagnostic information may indicate a diagnosis result of the user on the target subject. For example, the diagnostic information may include one or more diseases diagnosed by the user, one or more lesion regions diagnosed by the user, etc. The profile information may refer to supplementary information relating to the target subject, such as, name information, identity information, gender information, age information, height information, weight information, temperature information, medical history information, allergy information, etc. Merely by way of example, a motor cortex may include a primary motor area (M1), a premotor cortex (PMC), and a supplementary motor area (SMA). The motor cortex may be involved in motor planning and motor execution. A subcortical cerebral infarction lesion can cause damage and remodeling of the remote motor cortex, which is related to the degree of motor function recovery. Therefore, when a patient with the cerebral infarction in a rehabilitation process needs to be scanned, "cranial brain" may be input as the location information, and "rehabilitation assessment of cerebral infarction" may be input as the diagnostic information. As another example, when a patient with an acute stroke needs to be scanned, "brain portion" and/or "stroke" may be input as the location information.

In some embodiments, the clinical information may include first information of a first type, second information of a second type, and third information of a third type. The first type may refer to a type of information associated with requirement(s) of the target subject. For example, the first information of the first type may include the symptom information. The second type may refer to a type of information associated with requirement(s) of the user. For example, the second information of the second type may include the diagnostic information and the location information. The third type may refer to a type of information for supplement. For example, the third information of the third type may include the profile information.

In some embodiments, the user interface may further include one or more input items for the user to input user information. The user information may include identity information, habit information (e.g., a clarity requirement, a viewing direction), etc., of the user. By inputting the user information, differences between users may be considered. Therefore, a subsequent processing on the clinical information may be performed based on user information, which can better satisfy user's preference and improve the user experience.

Merely by way of example, referring to FIG. 7, FIG. 7 is a schematic diagram illustrating an exemplary user terminal 700 according to some embodiments of the present disclosure. As shown in FIG. 7, the user terminal 700 may include the mouse 710, the keyboard 720, and the display device 730. A user interface 740 may be displayed by the display device 730. The user interface 740 may include a plurality of regions (e.g., 742, 744, 746) and a button "START" 750. The region 742 may be used to display historical data (e.g., a previous scanning result) of a target subject. The historical data may be used as reference data for the scan, which can improve the accuracy of the inputted clinical information. The region 744 may be used to display a human body model corresponding to the target subject, so as to display a physical condition of the target subject. The region 746 may be used to display clinical information relating to the target subject. In some embodiments, the region 746 may display three input items for a user to input the clinical information relating to the target subject. As illustrated in FIG. 7, an input item 7462 may be used to input symptom information, an input item 7464 may be used to input diagnostic information, and an input item 7466 may be used to input location information relating to an ROI of the target subject (e.g., a region to be scanned). A region 748 may be used to input and/or display user information. The button "START" 750 may be used to send an instruction indicating that the clinical information relating to the target subject has been input, and subsequent operation(s) can be performed. For example, when the button "START" 750 is clicked, the process 300 may proceed to operations 304-308.

In 304, the processing device 140 (e.g., the receiving module 220) may receive, from the user terminal, the clinical information relating to the target subject.

In some embodiments, after the user interface is displayed, the user may input the clinical information into the user terminal through an input device. Exemplary input devices may include a keyboard, a mouse, a touch screen, a microphone, an augmented reality (AR) device, a projection device, or the like, or a combination thereof. For example, the user may perform a voice input to input the clinical information through the microphone. As another example, the user may perform a hand input to input the clinical information through the touch screen or the keyboard. As still another example, the user may perform an interaction operation to input the clinical information through the augmented reality device and/or the projection device. Through the input device, the user may remotely input the clinical information. For example, the user may input the clinical information in an operation room other than an asepsis room where the target subject and the medical device are located, which can achieve an aseptic operation, thereby improving a security of the scan.

In some embodiments, the processing device 140 may receive, from the user terminal, the clinical information relating to the target subject. For example, the processing device 140 may retrieve the clinical information relating to the target subject from the user terminal or a storage device (e.g., the storage device 150) where the user terminal stores the clinical information. In some embodiments, the processing device 140 may retrieve part of the clinical information from a storage device of the imaging system 100.

In 306, the processing device 140 (e.g., the determination module 230) may determine, based on the clinical information using a scanning parameter determination model, recommended values of scanning parameters to be used in a scan of the target subject. The scanning parameter determination model may be a trained machine learning model.

A recommended value of a scanning parameter may refer to a value that the scanning parameter can be set as during the scan of the target subject. In some embodiments, the processing device 140 may determine the recommended values of the scanning parameters using the scanning parameter determination model. For example, the processing device 140 may input the clinical information relating to the target subject into the scanning parameter determination model, and the scanning parameter determination model may output the recommended values of the scanning parameters.

The scanning parameters may refer to parameters in scanning protocol(s) used to direct the scan of the target subject. Exemplary scanning parameters may include parameters relating to RF pulses (e.g., the number of excitations (NEX), a bandwidth, etc.) emitted by an RF coil, parameters relating to a gradient field generated by a gradients coil, parameters relating to MR signals (e.g., an echo time (TE), an echo train length (ETL), a spin echo type, the number of phases), a slice thickness, an imaging type (e.g., T1 weighted imaging, T2 weighted imaging, proton density-weighted imaging, etc.), an acquisition time (TA), an inversion time, a repetition time (TR), oversampling, a fat suppression, a saturation band, or the like, or any combination thereof.

The scanning protocol(s) may be used to direct the medical device to scan the target subject to obtain a scanning result (e.g., scanning data). For example, the processing device 140 may scan the target subject based on the scanning protocol(s). In some embodiments, the scanning protocol(s) may include the scanning parameters and corresponding values. In some embodiments, values of at least one scanning parameter may be different for different scanning protocols. Exemplary scanning protocols may include a free induction decay (FID) sequence, a spin-echo (SE) sequence, an inversion recovery (IR) sequence, a gradient echo (GRE) sequence, an echo-planar imaging (EPI) sequence, a fast spin-echo (FSE) sequence, a fluid-attenuated inversion recovery (FLAIR) sequence, a diffusion-weighted imaging (DWI) sequence, or the like, or any combination thereof.

In some embodiments, the processing device 140 may determine the scanning protocol(s) to be used in the scan of the target subject based on the recommended values of the scanning parameters. For example, the processing device 140 may determine the scanning protocol as gre_scout, epi_dwi_tra, t2_fse_tra, t2_fse_flair_tra_fs, t1_se_tra, etc., based on the recommended values of the scanning parameters. For illustration purposes, in the present disclosure, "determine the scanning protocol(s) to be used in the scan of the target subject based on the recommended values of the scanning parameters, and scanning the target subject based on the scanning protocol(s)" may be referred to as "scanning the target subject based on the recommended values of the scanning parameters" for brevity.

The scanning parameter determination model may be configured to determine the recommended values of the scanning parameters to be used in the scan of the target subject based on a model input. In some embodiments, the scanning parameter determination model may be the machine learning model, such as, a deep learning network model, a convolutional neural networks (CNN) model, a deep belief network (DBN) model, a stacked auto-encoder network (SAE) model, or the like, or any combination thereof.

In some embodiments, the processing device 140 may generate the scanning parameter determination model by training an initial model using a plurality of training samples. In some embodiments, the initial model may be an initial machine learning model. Each of the plurality of training samples may include sample clinical information relating to a sample subject and ground truth values of the scanning parameters. More descriptions regarding the generation of the scanning parameter determination model may be found in elsewhere in the present disclosure (e.g., FIG. 4 and the descriptions thereof).

In some embodiments, the processing device 140 may further update the recommended values of the scanning parameters. For example, the processing device 140 may obtain reference data associated with a plurality of reference scans. The reference data associated with each reference scan may include reference values of the scanning parameters used in the reference scan. The processing device 140 may determine whether a difference between the recommended values and the reference values of the scanning parameters satisfies a difference condition. If the difference does not satisfy the difference condition, the processing device 140 may update the recommended values of the scanning parameters based on the reference data. More descriptions regarding the update of the recommended values of the scanning parameters may be found elsewhere in the present disclosure. See, e.g., FIG. 5 and relevant descriptions thereof.

In some embodiments, the scanning parameters to be used may include one or more first scanning parameters of a first type and one or more second scanning parameters of a second type. Accordingly, the scanning parameter determination model may include a first scanning parameter determination model and a second scanning parameter determination model. The processing device 140 may determine the recommended value of each first scanning parameter based on a first portion of the clinical information using the first scanning parameter determination model, and determine the recommended value of each second scanning parameter based on a second portion of the clinical information using the second scanning parameter determination model. For example, the one or more first scanning parameters of the first type may be more associated with the symptom information of the target subject, and the one or more second scanning parameters of the second type may be more associated with the location of the ROI of the target subject. The first portion of the clinical information may include the symptom information. The second portion of the clinical information may include the location information. Optionally, the first portion and second portion of the clinical information may further include other information, such as the diagnostic information, the profile information, etc.

In some embodiments, the processing device 140 may divide the scanning parameters into the one or more first scanning parameters of the first type and the one or more second scanning parameters of the second type based on historical data. For example, a first reference model and a second reference model may be generated. The input of the first reference model may include historical symptom information and historical profile information corresponding to a historical scan, and the output of the first reference model may include first predicted values of the scanning parameters. The input of the second reference model may include historical diagnostic information, historical location information, and the historical profile information corresponding to the historical scan, and the output of the second reference model may include second predicted values of the scanning parameters. For each of the scanning parameters, the processing device 140 may compare a first difference between the first predicted value and a historical value of the scanning parameter and a second difference between the second predicted value and the historical value of the scanning parameter. If the first difference exceeds the second difference, the processing device 140 may determine the scanning parameter as one of the one or more second scanning parameters of the second type. If the first difference does not exceed the second difference, the processing device 140 may determine the scanning parameter as one of the one or more first scanning parameters of the first type.

Figure 4:
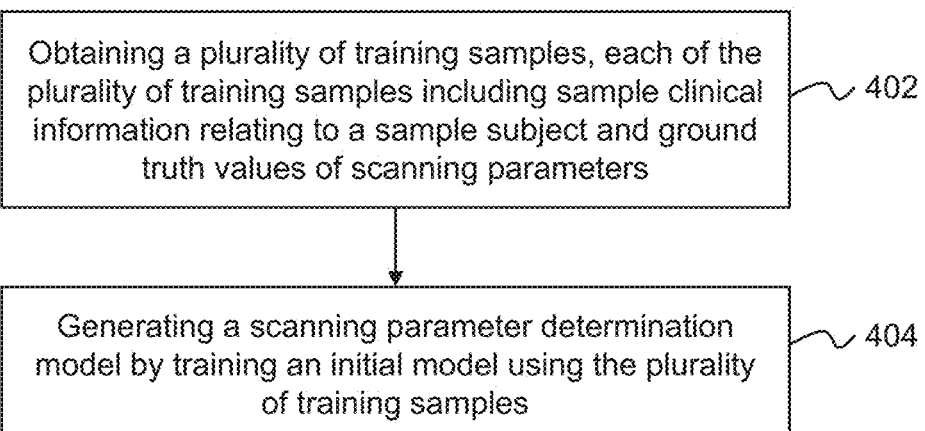
FIG. 4 is a flowchart illustrating an exemplary process for generating a scanning parameter determination model according to some embodiments of the present disclosure.

In some embodiments, the first scanning parameter determination model and/or the second scanning parameter determination model may be trained in a similar manner as how the scanning parameter determination model is obtained as described in the present disclosure (e.g., FIG. 4). For example, the processing device 140 may generate the first scanning parameter determination model by training the initial model using a plurality of first training samples. Each of the plurality of first training samples may include a first portion of the sample clinical information relating to the sample subject and the ground truth values of the first scanning parameters. Similarly, the processing device 140 may generate the second scanning parameter determination model by training the initial model using a plurality of second training samples. Each of the plurality of second training samples may include a second portion of the sample clinical information relating to the sample subject and the ground truth values of the second scanning parameters.

The scan parameter determination model may be established by taking historical use data of medical devices (e.g., an MRI device), medical system data, clinical guidelines and normative documents, etc., as input items, and analyzing and learning these data files, so as to establish a matching relationship between patient information and requirements of the medical scanning. For example, in view of the symptom information of the target subject, a first correlation model between the symptom information and scanning requirements may be established by analyzing that different symptom information corresponds to the scanning requirements, and then a second correlation model between the scanning requirements and scanning parts may be established by analyzing that different scanning requirements correspond to the scanning parts. Finally, a third correlation model between the scanning parameters (or the scanning protocols) and scanning parts may be established by analyzing the scanning parameters (or the scanning protocols) that need to be used when performing scanning of various functional technical categories for each of the scanning parts. Through the first correlation model, the second correlation model, and the third correlation model, a correlation relationship between the patient information and the scanning parameters may be established. It should be noted that the training is provided for the purposes of illustration, and is not intended to limit the scope of the present disclosure. For example, the scan parameter determination model may be established by using the historical use data of medical devices (e.g., an MRI device), the medical system data, the clinical guidelines and normative documents, etc., as input items of a neural network model, and optimizing the neural network model based on evaluations of scanning results of users during the use of the medical device. The optimized neural network model may be used as the scanning parameter determination model to act on a next scan of the medical device.

In 308, the processing device 140 (e.g., the obtaining module 240) may obtain a scanning result of the target subject based on the recommended values of the scanning parameters.

The scanning result may include scanning data that is collected by a medical device (e.g., the medical device 110) during the scan performed based on the recommended values of the scanning parameters. For example, the scanning result may include a medical image reconstructed based on the scanning data.

In some embodiments, the scanning result may further include analysis on the medical image and/or the scanning data. For example, the processing device 140 may perform a structural analysis and/or a functional analysis on the medical image and/or the scanning data. For instance, for a patient with the cerebral infarction in a rehabilitation process, the structural analysis may include gray matter volume in bilateral SMA (positively correlated with the degree of motor function recovery), gray matter volume in M1 on the same side of the lesion (the degree of atrophy is related to the degree of motor function recovery), gray matter volume in bilateral M1 and PMC on the lesion side (when decreasing, need to prompt that there is structural damage in the motor cortex remote from the lesion), and diffusion tensor imaging (DTI) imaging fiber bundles (used to determine the degree of damage to nerve connections, that can be used to determine anatomical connection damage between the corticospinal tract on the affected side and the bilateral M1, and the degree of damage to the corticospinal tract is related to the recovery of motor function after the cerebral infarction). The functional analysis may include determining the activation and enhancement on the lesion side, comparing the activation and enhancement with reference data of non-patient subjects, and comparing the activation and enhancement with a previous scanning result to determine whether the brain functional connection is gradually recovering, and whether it is possible to recover. As another example, the processing device 140 may perform an image segmentation and a parameter quantification on the medical image. For instance, the parameter quantification may include a tissue contrast, an anatomical structure, a spatial location, tissue component analysis and quantification, function quantification and analysis, etc. Accordingly, when the user selects a certain anatomical structure or tissue component to display, the processing device 140 may display the scanning result corresponding to the certain anatomical structure or tissue component on the display interface.

In some embodiments, the scanning result may further include reference data, such as, data of a healthy subject. Therefore, the target subject can intuitively determine a difference between the scanning result and the reference data, which reduces the difficulty of understanding of the scanning result.

In some embodiments, the processing device 140 may dynamically obtain the scanning result during the scan of the target subject. For example, the processing device 140 may uninterruptedly obtain the scanning data, and update the scanning result by reconstructing and/or analyzing the obtained scanning data. Therefore, the processing device 140 may adjust the scan of the subject in real time, thereby improving the efficiency and accuracy of the scan.

In some embodiments, the processing device 140 may display the scanning result on a display interface. The display interface may also be displayed by the user terminal (e.g., the terminal(s) 130). For example, the display interface may be displayed by the user terminal as an application or a website. As another example, the display interface may be an interface displayed on a projection surface projected by a projection device or an AR device. In some embodiments, the display interface may include a plurality of regions to display the scanning result. A size and a location of each of the plurality of regions may be adjusted based on an instruction input by the user. For example, the user may perform operations (e.g., a freezing operation, a translation operation, a rotation operation, an enlargement operation, etc.) on the each of the plurality of regions. In some embodiments, the user may move (e.g., translate, rotate, etc.) the scanning result (e.g., the medical image) on the display interface.

In some embodiments, the processing device 140 may determine whether the scanning result satisfies a scanning condition. The scanning condition may relate to, for example, the requirement(s) of the user, the requirement(s) of the target subject, the quality of the scanning result, etc. For example, if the scanning result includes the ROI(s) specified in the clinical information, the processing device 140 may determine that the scanning result satisfies the scanning condition. As another example, if the scanning result does not include the ROI(s) in the clinical information, the processing device 140 may determine that the scanning result does not satisfy the scanning condition.

If the scanning result does not satisfy the scanning condition, the processing device 140 may update the clinical information based on the scanning result. For example, the processing device 140 may display the user interface for the user to update the clinical information relating to the target subject. As another example, the processing device 140 may display a supplementary interface for updating the clinical information. The supplementary interface may be configured to perform an updated operation (e.g., a modification operation, an input operation, a removal operation, etc.) on the original clinical information corresponding to the one or more input items. For example, the supplementary interface may be suspended and displayed on the display interface, so that the user can update the clinical information in combination with the scanning result on the display interface.

In some embodiments, the user may manually update the clinical information relating to the target subject. For example, the display interface may include a supplementary button. The user may click the supplementary button to direct the user terminal to display the supplementary interface, and update the clinical information via the supplementary interface. As another example, the user may select a portion of the target subject on the display interface, and an option for selecting whether a local scan needs to be performed on the portion may be triggered.

In some embodiments, after the clinical information is updated, the processing device 140 may proceed to operations 304-308 again. That is, the processing device 140 may receive the updated clinical information, determine updated values of the scanning parameters based on the updated clinical information using the scanning parameter determination model, and obtain an updated scanning result of the target subject based on the updated values of the scanning parameters. In some embodiments, the processing device 140 may replace the scanning result with the updated scanning result, and display the updated scanning result on the display interface.

In some embodiments, the processing device 140 may obtain a fused scanning result by fusing the scanning result and the updated scanning result. For example, the processing device 140 may obtain a full-body scanning result of the target subject by fusing scanning results of the target subject in different scan directions.

Figure 8:
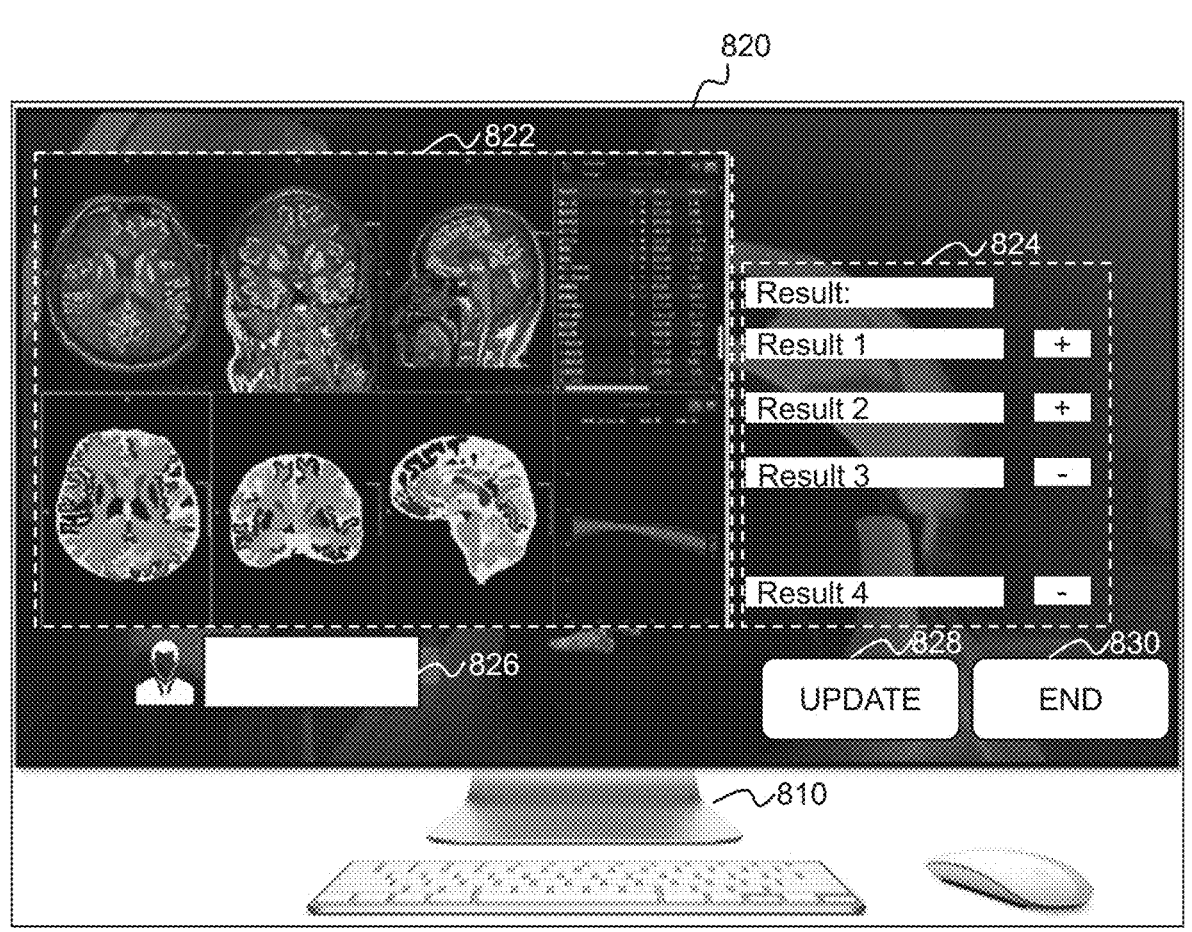
FIG. 8 is a schematic diagram illustrating an exemplary user terminal according to some embodiments of the present disclosure.

Merely by way of example, referring to FIG. 8, FIG. 8 is a schematic diagram illustrating an exemplary user terminal 800 according to some embodiments of the present disclosure. As shown in FIG. 8, the user terminal 800 may include a display device 810. A display interface 820 may be implemented on the display device 810. The display interface 820 may include a region 822 displaying medical images, a region 824 displaying a diagnostic result, a region 826 displaying user information, a button "UPDATE" 828, and a button "END" 830. The button "UPDATE" 828 may be used to send an instruction indicating that the clinical information needs to be updated. For example, when the button "UPDATE" 828 is clicked, the supplementary interface may be displayed. The button "END" 830 may be used to send an instruction indicating that the scan has been finished. For example, when the button "END" 830 is clicked, the display interface may be closed, and a report relating to the target subject may be generated. The report may include the scanning result (e.g., the medical image, the updated medical image, the analysis on the medical image and/or the updated medical image, etc.) and/or a comprehensive conclusion. For example, as shown in FIG. 8, the target subject may include a disease "Result 1" and/or a disease "Result 2," without a disease "Result 3" and a disease "Result 4." A symbol "+" may indicate that the target subject includes the corresponding result, and a symbol "−" may indicate that the target subject does not include the corresponding result. Therefore, the comprehensive conclusion may be "Needs to be treated."

In some embodiments, the processing device 140 may determine, during the scan of the target subject, whether an abnormal condition occurs. The abnormal condition may refer to a condition that the scan needs to be adjusted. For example, the processing device 140 may obtain one or more detection images of the target subject captured during the scan of the target subject. The processing device 140 may obtain a determination result by determining whether the one or more detection images of the target subject satisfy the abnormal condition. Further, the processing device 140 may determine whether the abnormal condition occurs based on the determination result. If the abnormal condition occurs, the processing device 140 may determine a processing strategy of the abnormal condition based on the one or more detection images of the target subject. More descriptions regarding the determination of whether the abnormal condition occurs and the processing strategy may be found elsewhere in the present disclosure. See, e.g., FIG. 6 and relevant descriptions thereof.

According to some embodiments of the present disclosure, the recommended values of the scanning parameters to be used in the scan of the target subject may be determined based on the clinical information using the scanning parameter determination model, and the scanning result of the target subject may be obtained based on the recommended values of the scanning parameters. The user needs to perform no operation such as scanning protocol arrangement, posture monitoring, etc., which can improve the operation convenience of the medical device and the efficiency of the scanning. Therefore, the imaging system (e.g., the imaging system 100) can intelligently and automatically perform acquisition, reconstruction, and analysis, which can reduce workloads of the user, and improve the user experience.

In addition, by introducing the machine learning model, the imaging system can automatically determine and/or update the recommended values of the scanning parameters and process the abnormal condition. Moreover, possible abnormal conditions that occur during the scan may be detected and processed automatically. Therefore, the user does not need to constantly monitor the implementation of the scan, thereby improving the reliability and consistency of the scanning results. For example, a clinician who has no experience in operating the imaging system can perform a scan on the target subject through the imaging system, and obtain a scanning result that satisfies requirements of the clinician.

It should be noted that the descriptions of the process 300 are provided for the purposes of illustration, and are not intended to limit the scope of the present disclosure. For persons having ordinary skills in the art, various variations and modifications may be conducted under the teaching of the present disclosure. However, those variations and modifications may not depart from the protection of the present disclosure. In some embodiments, in order to ensure the safety of the clinical information input, the processing device 140 may perform a recognition and/or verification on the user before operation 302 or operation 304. For example, the processing device 140 may determine whether an input voice matches a predetermined voice of the user. If the input voice matches the predetermined voice of the user, the processing device 140 may receive the clinical information relating to the target subject. If the input voice does not match the predetermined voice of the user, the processing device 140 may reject the input clinical information.

FIG. 4 is a flowchart illustrating an exemplary process 400 for generating a scanning parameter determination model according to some embodiments of the present disclosure. In some embodiments, the process 400 may be performed to achieve at least part of operation 306 as described in connection with FIG. 3.

In 402, the processing device 140 (e.g., the training module 250) may obtain a plurality of training samples. Each of the plurality of training samples including sample clinical information relating to a sample subject and ground truth values of scanning parameters.

In some embodiments, each of at least some of the plurality of training samples may be obtained from historical clinical data of one or more sample subjects. For example, the processing device 140 may obtain the training sample (including the sample clinical information relating to the sample subject and the corresponding ground truth values of the scanning parameters) from a user terminal (e.g., the terminal(s) 130) or a storage device (e.g., the storage device 150, a scanning parameter database, or an external storage). The scanning parameter database may be established to store historical data, such as, historical symptom information, historical scanning information, historical location information, historical scanning parameters (scanning protocols), etc.

In some embodiments, for a training sample, the processing device 140 may obtain the sample clinical information relating to the sample subject of the training sample from a user terminal (e.g., the terminal(s) 130) or a storage device (e.g., the storage device 150, a database, or an external storage). For example, the sample clinical information relating to the sample subject may be obtained in a similar manner as how the clinical information is received as described in operation 304.

In some embodiments, the ground truth values of the scanning parameters corresponding to the sample clinical information relating to the sample subject may be determined manually. For example, a user may manually determine the ground truth values of the scanning parameters corresponding to the sample clinical information.

In some embodiments, the plurality of training samples may further include clinical guidelines and normative documents. Therefore, features required for disease identification may be determined, which can intelligently plan scanning parameters such as scanning procedures, thereby improving the efficiency of the scan.

In 404, the processing device 140 (e.g., the training module 250) may generate a scanning parameter determination model by training an initial model using the plurality of training samples.

The training of the initial model may include an iterative process. The plurality of training samples may be used to iteratively update model parameter(s) of the initial model until a termination condition is satisfied. Exemplary termination conditions may include that a value of a loss function corresponding to the initial model is below a threshold value, a difference of values of the loss function obtained in a previous iteration and the current iteration is within a threshold value, a certain count of iterations has been performed, etc. For example, in a current iteration, sample clinical information relating to a sample subject may be input into the initial model corresponding to the current iteration, and the initial model may output a prediction result. Then, a value of the loss function may be determined to measure a difference between the prediction result and the label (e.g., ground truth values of the scanning parameters). If it is determined that the termination condition is satisfied in the current iteration, the initial model may be designated as the scanning parameter determination model; otherwise, the initial model may be further updated based on the value of the loss function.

FIG. 5 is a flowchart illustrating an exemplary process 500 for updating recommended values of scanning parameters according to some embodiments of the present disclosure. In some embodiments, the process 500 may be performed to achieve at least part of operation 306 as described in connection with FIG. 3.

In 502, the processing device 140 (e.g., the determination module 230) may obtain reference data associated with a plurality of reference scans. The reference data associated with each reference scan may include reference values of scanning parameters used in the reference scan.

The reference data may relate to one or more reference subjects that match with the target subject, for example, a subject who is of the same type as the target subject and have similar features to the target subject. In some embodiments, the processing device 140 may determine the one or more reference subjects from a storage device or a subject database. For example, for each subject in a subject database, the processing device 140 may generate a feature vector based on feature data (e.g., symptom information, diagnostic information, location information of ROI(s), etc.) of the subject. The processing device 140 may determine one or more reference feature vectors from feature vectors of the subjects in the subject database based on a similarity algorithm and a target feature vector of the target subject, and designate one or more subjects corresponding to the one or more reference feature vectors as the one or more reference subjects. For example, the similarity degree between each reference feature vector and the target feature vector may be smaller than a threshold.

For each of the one or more reference subjects, the processing device 140 may determine the reference scan of the reference subject. For example, the processing device 140 may determine the reference scan based on a scan type and a scanning part of the target subject. That is, if a scan type and a scanning part of a historical scan of a reference subject are the same as the scan type and the scanning part of the target subject, respectively, the processing device 140 may determine the historical scan of the reference subject as a reference scan, and designate data associated with the historical scan of the reference subject as a portion of the reference data.

In 504, the processing device 140 (e.g., the determination module 230) may determine whether a difference between recommended values and the reference values of the scanning parameters satisfies a difference condition.

In some embodiments, for each of the scanning parameters, the processing device 140 may determine a mean reference value for the plurality of reference scans. Accordingly, the difference may be generated between the recommended values and the mean reference values.

In some embodiments, the difference condition may include that a maximum difference of the scanning parameters is less than a maximum threshold, a mean difference of the scanning parameters is less than a mean threshold, etc. For example, for each of the scanning parameters, the processing device 140 may determine a difference between the recommended value and the mean reference value. Further, the processing device 140 may determine a maximum difference among the differences, and determine whether the maximum difference is less than the maximum threshold. If the maximum difference is less than the maximum threshold, the processing device 140 may determine that the difference satisfies the difference condition. If the maximum difference is equal to or larger than the maximum threshold, the processing device 140 may determine that the difference does not satisfy the difference condition. Alternatively, the processing device 140 may determine a mean difference for the differences, and determine whether the mean difference is less than the mean threshold. If the mean difference is less than the mean threshold, the processing device 140 may determine that the difference satisfies the difference condition. If the mean difference is equal to or larger than the mean threshold, the processing device 140 may determine that the difference does not satisfy the difference condition. The maximum threshold and/or the mean threshold may be determined based on the system default setting or set manually by the user.

If the difference satisfies the difference condition, the processing device 140 may end the process 500 or output the recommended values of the scanning parameters. That is, the recommended values of the scanning parameters do not need to be updated.

If the difference does not satisfy the difference condition, the process 500 may proceed to operation 506.

In 506, the processing device 140 (e.g., the determination module 230) may update the recommended values of the scanning parameters based on the reference data.

For example, for each of the scanning parameters, the processing device 140 may obtain an updated value by determining a weighted average between the recommended value and the mean reference value or modifying the recommended value based on the mean reference value.

According to some embodiments, the recommended values of the scanning parameters may be updated based on the reference data, which can check and/or adjust the recommended values, thereby improving the accuracy of the scanning parameter determination.

Figure 6:
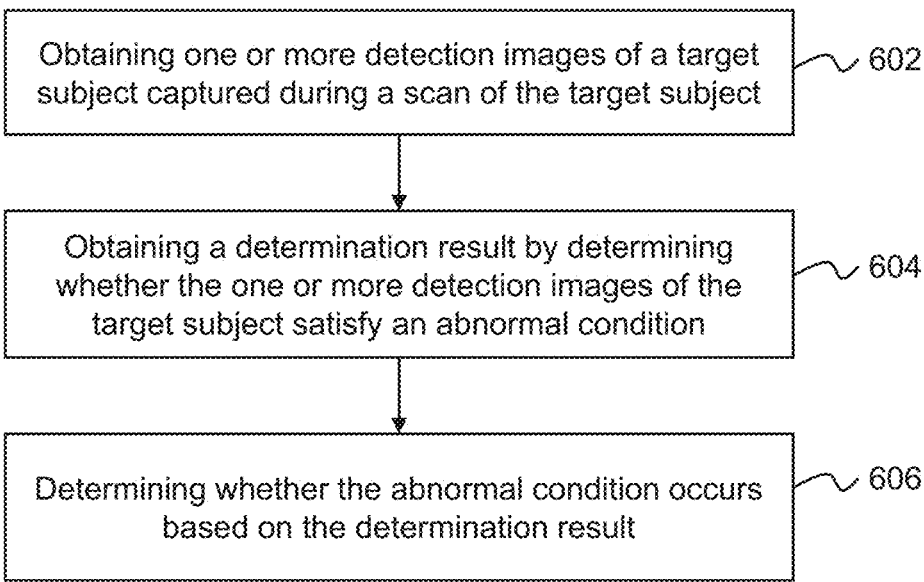
FIG. 6 is a flowchart illustrating an exemplary process for determining whether an abnormal condition occurs according to some embodiments of the present disclosure.

FIG. 6 is a flowchart illustrating an exemplary process 600 for determining whether an abnormal condition occurs according to some embodiments of the present disclosure. In some embodiments, the process 600 may be performed during the scan of the target subject to achieve at least part of operation 308 as described in connection with FIG. 3.

In 602, the processing device 140 (e.g., the obtaining module 240) may obtain one or more detection images of a target subject captured during the scan of the target subject.

A detection image may be configured to provide posture information and/or physiological information of the target subject during the scan of the target subject. In some embodiments, the one or more detection images may be captured through one or more sensors. Exemplary sensors may include an optical sensor, a radar sensor, a ranging device, a time-of-flight (TOF) device, a structured light scanner, a camera, a cardiac sensor (e.g., an ECG sensor), a respiratory sensor, a temperature sensor, a blood pressure sensor, or the like, or any combination thereof. For example, the optical sensor may capture optical images including the posture information of the target subject during the scan of the target subject. As another example, the temperature sensor may capture thermal images including the physiological information (e.g., temperature information) of the target subject during the scan of the target subject.

In some embodiments, the processing device 140 may obtain the one or more detection images of the target subject from the one or more sensors or a storage device (e.g., the storage device 150) that stores the one or more detection images.

In 604, the processing device 140 (e.g., the determination module 230) may obtain a determination result by determining whether the one or more detection images of the target subject satisfy an abnormal condition.

The abnormal condition may refer to a condition that the scan needs to be adjusted. In some embodiments, the abnormal condition may include that the physiological information is abnormal (such as, the change in a temperature is larger than a temperature change threshold, the change in a blood pressure is larger than a blood pressure change threshold, a heartbeat rate is larger than a heartbeat threshold, etc.), a motion displacement of the target subject exceeds a displacement threshold, a breath-holding time is less than a predetermined period, etc.

The determination result may refer to a result indicating whether the one or more detection images of the target subject satisfy the abnormal condition. In some embodiments, the processing device 140 may obtain the determination result based on the posture information and/or physiological information. For example, the processing device 140 may determine the motion displacement of the target subject during the scan of the target subject based on the one or more detection images, and further determine whether the motion displacement of the target subject exceeds the displacement threshold to obtain the determination result.

In 606, the processing device 140 (e.g., the determination module 230) may determine whether the abnormal condition occurs based on the determination result.

If the determination result indicates that the one or more detection images of the target subject do not satisfy the abnormal condition, the processing device 140 may determine that no abnormal condition occurs. If the determination result indicates that the one or more detection images of the target subject satisfy the abnormal condition, the processing device 140 may determine that the abnormal condition occurs.

In some embodiments, in response to determining that the abnormal condition occurs, the processing device 140 may determine a processing strategy of the abnormal condition based on the one or more detection images of the target subject. The processing strategy may be configured to process the abnormal condition. For example, if the abnormal condition includes a large motion displacement, the processing strategy may include prompting the target subject to keep still or move to an original position. As another example, if the abnormal condition includes that the change in the temperature is larger than the temperature change threshold, the change in the blood pressure is larger than the blood pressure change threshold, the heartbeat rate is larger than the heartbeat threshold, etc., the processing strategy may include reducing the scan time or ending the scan. As still another example, if the abnormal condition includes that the scanning parameter(s) need to be adjusted, the processing strategy may include adjusting the scanning parameter(s).

In some embodiments, the processing device 140 may determine the processing strategy based on the one or more detection images of the target subject using a processing strategy determination model. The processing strategy determination model may be a machine learning model. For example, the processing device 140 may input the one or more detection images of the target subject to the processing strategy determination model, and the processing strategy determination model may output the processing strategy. The processing strategy determination model may be obtained by training an initial model based on a plurality of training samples, wherein each of the plurality of training samples may include one or more sample detection images sample of a sample subject and a corresponding sample processing strategy. In some embodiments, each of at least a portion of the plurality of training samples may be obtained from historical processing data of one or more users.

Merely by way of example, the scan of the target subject may be divided into a plurality of sub-scans, and each of the plurality of sub-scans may correspond to at least one of the one or more detection images. For example, the processing device 140 may determine each sub-scan with five respiratory cycles, and obtain one or more detection images corresponding to the each sub-scan. For each of the plurality of sub-scans, the processing device 140 may determine whether an abnormal condition occurs during the sub-scan. For example, the processing device 140 may input the at least one detection image into an image analysis model, and the image analysis model may output whether the at least one detection image is different from a previous detection image and/or whether the abnormal condition occurs during the sub-scan. If the abnormal condition occurs during the sub-scan, the processing device 140 may update scanning parameters in a current sub-scan and remaining sub-scan(s).

According to some embodiments of the present disclosure, the one or more detection images of the target subject may be obtained, and whether the abnormal condition occurs may be automatically determined, which can improve the security of the scan. In addition, the processing strategy may be determined using a machine learning model, which can reduce the user intervention and improve the efficiency of the scan.

Processes 400-600 may be implemented in the imaging system 100 illustrated in FIG. 1. For example, the processes 400-600 may be stored in the storage device 150 in the form of instructions (e.g., an application), and invoked and/or executed by the processing device 140. The operations of the illustrated process are intended to be illustrative. It should be noted that the descriptions of the processes 400-600 are provided for the purposes of illustration, and are not intended to limit the scope of the present disclosure. For persons having ordinary skills in the art, various variations and modifications may be conducted under the teaching of the present disclosure. For example, the processes 400-600 may be accomplished with one or more additional operations not described, and/or without one or more of the operations discussed. Additionally, the order in which the operations of the processes 400-600 is not intended to be limiting. However, those variations and modifications may not depart from the protection of the present disclosure.

Figure 9:
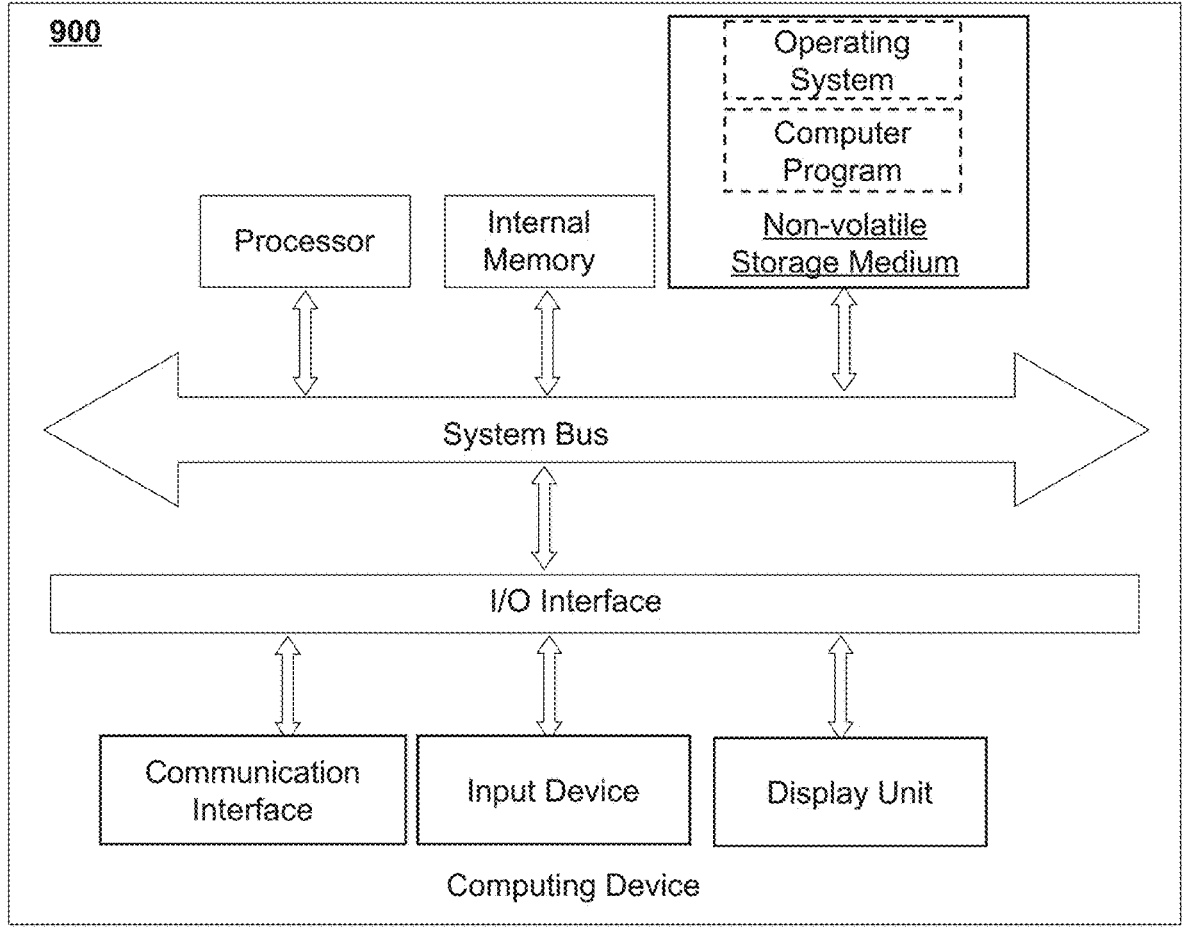
FIG. 9 is a schematic diagram illustrating an exemplary computing device according to some embodiments of the present disclosure.

FIG. 9 is a schematic diagram illustrating an exemplary computing device 900 according to some embodiments of the present disclosure.

In some embodiments, one or more components of the imaging system 90 may be implemented on the computing device 900. For example, a processing device 140 may be implemented on the computing device 900 and configured to implement the functions and/or methods disclosed in the present disclosure.

The computing device 900 may include any components used to implement the imaging system 100 described in the present disclosure. For example, the processing device 140 may be implemented through hardware, software programs, firmware, or any combination thereof, on the computing device 900. For illustration purposes, only one computer is described in FIG. 9, but computing functions related to the imaging system 100 described in the present disclosure may be implemented in a distributed fashion by a group of similar platforms to spread the processing load of the imaging system 100.

The computing device 900 may include a processor (e.g., a central processing unit (CPU)), a memory, a communication interface, a display unit, and an input device connected by a system bus. The processor of the computing device 900 may be used to provide computing and control capabilities. The memory of the computing device 900 may include a non-volatile storage medium, an internal memory. The non-volatile storage medium may store an operating system and a computer program. The internal memory may provide an environment for the execution of the operating system and the computer program in the non-volatile storage medium. The communication interface of the computing device 900 may be used for wired or wireless communication with an external terminal. The wireless communication may be realized through Wi-Fi, a mobile cellular network, a near field communication (NFC), etc. When the computer program is executed by the processor, a method for determining feature points may be implemented. The display unit of the computing device 900 may include a liquid crystal display screen or an electronic ink display screen. The input device of the computing device 900 may include a touch layer covered on the display unit, a device (e.g., a button, a trackball, a touchpad, etc.) set on the housing of the computing device 900, an external keyboard, an external trackpad, an external mouse, etc.

Merely for illustration, only one processor is described in FIG. 9. However, it should be noted that the computing device 900 in the present disclosure may also include multiple processors. Thus operations and/or method steps that are performed by one processor as described in the present disclosure may also be jointly or separately performed by the multiple processors. For example, if the processor of the computing device 900 in the present disclosure executes both operation A and operation B, it should be understood that operation A and operation B may also be performed by two or more different processors jointly or separately (e.g., a first processor executes operation A and a second processor executes operation B, or the first and second processors jointly execute operations A and B).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, device, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for scanning parameter determination implemented on a computing device having at least one processor and at least one storage device, the method comprising:
   displaying, via a user terminal, a user interface including one or more input items for a user to input clinical information relating to a target subject, the clinical information at least including symptom information;
   receiving, from the user terminal, the clinical information relating to the target subject; and
   determining, based on the clinical information using a scanning parameter determination model, recommended values of scanning parameters to be used in a scan of the target subject, the scanning parameter determination model being a trained machine learning model.

2. The method of claim 1, wherein the clinical information further includes at least one of diagnostic information of the target subject, location information of a region of interest of the target subject, or profile information of the target subject.

3. The method of claim 1, further comprising:
   obtaining a scanning result of the target subject based on the recommended values of the scanning parameters;
   determining whether the scanning result satisfies a scanning condition; and
   in response to determining that the scanning result does not satisfy the scanning condition, updating the clinical information based on the scanning result.

4. The method of claim 1, further comprising:
   determining, during the scan of the target subject, whether an abnormal condition occurs.

5. The method of claim 4, wherein the determining whether an abnormal condition occurs includes:
   obtaining one or more detection images of the target subject captured during the scan of the target subject;
   obtaining a determination result by determining whether the one or more detection images of the target subject satisfy the abnormal condition; and
   determining whether the abnormal condition occurs based on the determination result.

6. The method of claim 5, wherein the scan of the target subject is divided into a plurality of sub-scans, and each of the plurality of sub-scans corresponds to at least one of the one or more detection images.

7. The method of claim 5, further comprising:
   in response to determining that the abnormal condition occurs, determining a processing strategy of the abnormal condition based on the one or more detection images of the target subject.

8. The method of claim 1, further comprising:
   obtaining reference data associated with a plurality of reference scans, the reference data associated with each reference scan including reference values of the scanning parameters used in the reference scan;

determining whether a difference between the recommended values and the reference values of the scanning parameters satisfies a difference condition; and in response to determining that the difference does not satisfy the difference condition, updating the recommended values of the scanning parameters based on the reference data.

9. The method of claim 2, the scanning parameter determination model includes a first scanning parameter determination model and a second scanning parameter determination model, and the scanning parameters to be used includes one or more first scanning parameters of a first type and one or more second scanning parameters of a second type, wherein the determining recommended values of scanning parameters to be used in a scan of the target subject comprises:

determining the recommended value of each first scanning parameter based on a first portion of the clinical information using the first scanning parameter determination model; and determining the recommended value of each second scanning parameter based on a second portion of the clinical information using the second scanning parameter determination model.

10. The method of claim 1, wherein the scanning parameter determination model is generated according to a process including:

obtaining a plurality of training samples, each of the plurality of training samples including sample clinical information relating to a sample subject and ground truth values of the scanning parameters; and generating the scanning parameter determination model by training an initial model using the plurality of training samples.

11. A system for scanning parameter determination, comprising:

at least one storage device including a set of instructions; and at least one processor configured to communicate with the at least one storage device, wherein when executing the set of instructions, the at least one processor is configured to direct the system to perform operations including:

displaying, via a user terminal, a user interface including one or more input items for a user to input clinical information relating to a target subject, the clinical information at least including symptom information;

receiving, from the user terminal, the clinical information relating to the target subject; and determining, based on the clinical information using a scanning parameter determination model, recommended values of scanning parameters to be used in a scan of the target subject, the scanning parameter determination model being a trained machine learning model.

12. The system of claim 11, wherein the clinical information further includes at least one of diagnostic information of the target subject, location information of a region of interest of the target subject, or profile information of the target subject.

13. The system of claim 11, further comprising:

obtaining a scanning result of the target subject based on the recommended values of the scanning parameters;

determining whether the scanning result satisfies a scanning condition; and in response to determining that the scanning result does not satisfy the scanning condition, updating the clinical information based on the scanning result.

14. The system of claim 11, further comprising:

determining, during the scan of the target subject, whether an abnormal condition occurs.

15. The system of claim 14, wherein the determining whether an abnormal condition occurs includes:

obtaining one or more detection images of the target subject captured during the scan of the target subject;

obtaining a determination result by determining whether the one or more detection images of the target subject satisfy the abnormal condition; and determining whether the abnormal condition occurs based on the determination result.

16. The system of claim 15, wherein the scan of the target subject is divided into a plurality of sub-scans, and each of the plurality of sub-scans corresponds to at least one of the one or more detection images.

17. The system of claim 15, further comprising:

in response to determining that the abnormal condition occurs, determining a processing strategy of the abnormal condition based on the one or more detection images of the target subject.

18. The system of claim 11, further comprising:

obtaining reference data associated with a plurality of reference scans, the reference data associated with each reference scan including reference values of the scanning parameters used in the reference scan;

determining whether a difference between the recommended values and the reference values of the scanning parameters satisfies a difference condition; and in response to determining that the difference does not satisfy the difference condition, updating the recommended values of the scanning parameters based on the reference data.

19. The system of claim 12, the scanning parameter determination model includes a first scanning parameter determination model and a second scanning parameter determination model, and the scanning parameters to be used includes one or more first scanning parameters of a first type and one or more second scanning parameters of a second type, wherein the determining recommended values of scanning parameters to be used in a scan of the target subject comprises:

determining the recommended value of each first scanning parameter based on a first portion of the clinical information using the first scanning parameter determination model; and determining the recommended value of each second scanning parameter based on a second portion of the clinical information using the second scanning parameter determination model.

20. A non-transitory computer readable medium, comprising executable instructions that, when executed by at least one processor, direct the at least one processor to perform a method, the method comprising:

displaying, via a user terminal, a user interface including one or more input items for a user to input clinical information relating to a target subject, the clinical information at least including symptom information;

receiving, from the user terminal, the clinical information relating to the target subject; and determining, based on the clinical information using a scanning parameter determination model, recommended values of scanning parameters to be used in a scan of the target subject, the scanning parameter determination model being a trained machine learning model.

* * * * *